United States Patent
Govari et al.

(10) Patent No.: US 10,517,667 B2
(45) Date of Patent: Dec. 31, 2019

(54) CATHETER TIP WITH MICROELECTRODES

(71) Applicant: BIOSENSE WEBSTER (ISRAEL) LTD., Yokneam (IL)

(72) Inventors: Assaf Govari, Haifa (IL); Christopher Thomas Beeckler, Brea, CA (US); Rowan Olund Hettel, Pasadena, CA (US)

(73) Assignee: Biosense Webster (Israel) Ltd., Yokneam (IL)

( * ) Notice: Subject to any disclaimer, the term of this patent is extended or adjusted under 35 U.S.C. 154(b) by 814 days.

(21) Appl. No.: 14/279,682

(22) Filed: May 16, 2014

(65) Prior Publication Data

US 2015/0327921 A1 Nov. 19, 2015

(51) Int. Cl.
*A61B 5/04* (2006.01)
*A61B 18/18* (2006.01)
(Continued)

(52) U.S. Cl.
CPC .......... *A61B 18/1492* (2013.01); *A61B 5/042* (2013.01); *A61B 5/0422* (2013.01); *A61B 5/0538* (2013.01); *A61B 5/6852* (2013.01); *A61B 2018/00053* (2013.01); *A61B 2018/00351* (2013.01); *A61B 2018/00577* (2013.01); *A61B 2018/00839* (2013.01); *A61B 2018/1467* (2013.01); *A61B 2018/1497* (2013.01); *Y10T 29/49004* (2015.01)

(58) Field of Classification Search
CPC ...... A61B 18/1492; A61B 2018/00577; A61B 18/02; A61B 2018/0212; A61B 2018/00839; A61B 5/0422; A61B 5/6852; A61B 5/042; A61B 2018/00357; A61B 2218/002; A61B 5/01; A61B 2018/00821; A61B 2018/00863; A61N 1/00; A61N 1/06
USPC ............. 600/372–381, 508–509; 606/20–26; 607/115–119
See application file for complete search history.

(56) References Cited

U.S. PATENT DOCUMENTS 5,499,631 A   3/1996 Weiland
5,833,688 A   11/1998 Sieben et al.
(Continued)

FOREIGN PATENT DOCUMENTS

EP   2441408 A1   4/2012
WO  WO 2006/014966 A2   2/2006

OTHER PUBLICATIONS

European Communication dated May 10, 2017 from corresponding European Patent Application No. 15167813.3.
CN Office Action: Appln. No. 201510249718.9 dated Aug. 24, 2018.

*Primary Examiner* — Joseph A Stoklosa
*Assistant Examiner* — Brian M Antiskay
(74) *Attorney, Agent, or Firm* — Todd J. Burns

(57) ABSTRACT

Apparatus, having an insertion tube that is configured to be inserted into a body cavity. The apparatus also includes a distal tip connected to the insertion tube, the distal tip having an external surface and a cavity formed in the external surface, the cavity being surrounded by a region of the external surface having a curvature. The apparatus further includes a microelectrode configured to fit into the cavity so that a surface of the microelectrode is contoured, located and oriented to conform with the curvature of the region.

12 Claims, 3 Drawing Sheets

(51) Int. Cl.
*A61B 18/14* (2006.01)
*A61B 5/053* (2006.01)
*A61B 5/042* (2006.01)
*A61B 5/00* (2006.01)
*A61B 18/00* (2006.01)

(56) References Cited

U.S. PATENT DOCUMENTS

| | | | |
|---|---|---|---|
| 5,921,924 A * | 7/1999 | Avitall | A61B 5/0422 600/373 |
| 5,935,124 A | 8/1999 | Klumb et al. | |
| 5,957,961 A | 9/1999 | Maguire et al. | |
| 6,036,687 A * | 3/2000 | Laufer | A61B 18/08 604/113 |
| 6,049,737 A * | 4/2000 | Simpson | A61B 18/1492 607/119 |
| 6,162,184 A | 12/2000 | Swanson et al. | |
| 6,210,406 B1 | 4/2001 | Webster | |
| 6,217,573 B1 | 4/2001 | Webster | |
| 6,217,574 B1 | 4/2001 | Webster | |
| 6,582,425 B2 * | 6/2003 | Simpson | A61B 18/1492 606/32 |
| 6,799,064 B1 | 9/2004 | Hassett | |
| 7,047,068 B2 | 5/2006 | Haissaguerre | |
| 7,300,438 B2 | 11/2007 | Falwell et al. | |
| 7,306,594 B2 | 12/2007 | Collins et al. | |
| 7,727,229 B2 | 6/2010 | He et al. | |
| 7,850,685 B2 | 12/2010 | Kunis et al. | |
| 8,157,796 B2 | 4/2012 | Collins et al. | |
| 8,206,384 B2 | 6/2012 | Falwell et al. | |
| 8,273,084 B2 | 9/2012 | Kunis et al. | |
| 8,337,492 B2 | 12/2012 | Kunis et al. | |
| 8,388,549 B2 | 3/2013 | Paul et al. | |
| 8,414,579 B2 * | 4/2013 | Kim | A61B 18/18 606/33 |
| 8,449,539 B2 | 5/2013 | Wang et al. | |
| 8,456,182 B2 | 6/2013 | Bar-Tal et al. | |
| 8,460,285 B2 | 6/2013 | Wang et al. | |
| 8,475,448 B2 | 7/2013 | Sharareh et al. | |
| 8,600,472 B2 * | 12/2013 | Govari | A61B 5/0422 600/373 |
| 8,636,731 B2 | 1/2014 | Falwell et al. | |
| 8,668,686 B2 | 3/2014 | Govari et al. | |
| 2003/0229286 A1 * | 12/2003 | Lenker | A61B 8/12 600/462 |
| 2004/0092806 A1 * | 5/2004 | Sagon | A61B 5/0422 600/374 |
| 2004/0193152 A1 * | 9/2004 | Sutton | A61B 18/1477 606/48 |
| 2006/0253030 A1 | 11/2006 | Altmann et al. | |
| 2007/0016007 A1 | 1/2007 | Govari et al. | |
| 2008/0039790 A1 * | 2/2008 | Hasebe | A61B 18/04 604/113 |
| 2008/0234564 A1 * | 9/2008 | Beatty | A61B 5/0422 600/374 |
| 2010/0168557 A1 | 7/2010 | Deno et al. | |
| 2011/0106074 A1 | 5/2011 | Kunis et al. | |
| 2011/0130648 A1 | 6/2011 | Beeckler et al. | |
| 2012/0095362 A1 * | 4/2012 | Fang | A61B 18/1492 600/549 |
| 2013/0116688 A1 | 5/2013 | Kunis et al. | |
| 2014/0052119 A1 | 2/2014 | Stewart et al. | |
| 2014/0052120 A1 | 2/2014 | Benscoter et al. | |
| 2014/0058375 A1 | 2/2014 | Koblish | |
| 2014/0081262 A1 * | 3/2014 | Koblish | A61B 18/1492 606/41 |

* cited by examiner

CATHETER TIP WITH MICROELECTRODES

FIELD OF THE INVENTION

The present invention relates generally to catheters, and specifically to configuration of the catheter tip.

BACKGROUND OF THE INVENTION

Radiofrequency (RF) ablation of the heart is a procedure that is widely used to correct problematic cardiac conditions, such as atrial fibrillation. The procedure typically involves insertion of a catheter probe, having an electrode, into the heart, and ablating selected regions within the heart with RF energy transmitted via the electrode.

Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

SUMMARY OF THE INVENTION

An embodiment of the present invention provides apparatus, including:

an insertion tube, configured to be inserted into a body cavity;

a distal tip connected to the insertion tube, the distal tip having an external surface and a cavity formed in the external surface, the cavity being surrounded by a region of the external surface having a curvature; and a microelectrode configured to fit into the cavity so that a surface of the microelectrode is contoured, located and oriented to conform with the curvature of the region.

Typically, the external surface of the distal tip and the surface of the microelectrode are defined by a common equation.

In a disclosed embodiment the apparatus includes insulation located so as to electrically insulate the microelectrode from the distal tip.

In a further disclosed embodiment the apparatus includes at least one conductor, insulated from the distal tip, connected to the microelectrode and configured to convey an electropotential generated by the body cavity and detected by the microelectrode.

In a yet further disclosed embodiment the apparatus includes at least two conductors of two different materials connected at a junction to form a thermocouple, wherein the junction is connected to the microelectrode so as to provide a signal representative of a temperature of the microelectrode.

In an alternative embodiment the distal tip is configured to receive radiofrequency (RF) energy at an ablation frequency adapted to perform ablation on the body cavity. Typically, the microelectrode is configured to detect an electropotential at a lower frequency than the ablation frequency. The apparatus may include a high pass filter, configured to block the lower frequency and to pass the ablation frequency, coupling the microelectrode to the distal tip. The apparatus may also include a handle configured for a user of the apparatus to hold the insertion tube, wherein the high pass filter is located within the handle.

In a further alternative embodiment the external surface and the surface of the microelectrode have a common non-zero first principal curvature and a common second principal curvature equal to zero.

In a yet further alternative embodiment the external surface and the surface of the microelectrode have a common surface of revolution.

There is further provided, according to an embodiment of the present invention, a method, including:

providing an insertion tube that is configured to be inserted into a body cavity;

connecting a distal tip to the insertion tube, the distal tip having an external surface and a cavity formed in the external surface, the cavity being surrounded by a region of the external surface having a curvature; and fitting a microelectrode into the cavity so that a surface of the microelectrode is contoured, located and oriented to conform with the curvature of the region.

The present disclosure will be more fully understood from the following detailed description of the embodiments thereof, taken together with the drawings, in which:

DETAILED DESCRIPTION OF EMBODIMENTS

Overview

An embodiment of the present invention provides a catheter that may be used for performing a radiofrequency (RF) ablation procedure in a body cavity. The catheter comprises an insertion tube, which has at a distal end of the tube a distal tip that is configured to act as an electrode for the ablation. The distal tip, typically formed in a generally cup-like shape, has an external surface, and at least one cavity, typically six cavities, is formed in the external surface. Each cavity is surrounded by a respective region of the external surface, and each respective region has a respective curvature.

For each cavity there is a respective microelectrode configured to fit into the cavity. For a given microelectrode, an outer surface of the microelectrode is contoured to conform with the curvature of the region of the distal tip's outer surface surrounding the cavity. Each microelectrode and its cavity are configured so that when the microelectrode fits to the cavity, the microelectrode is located and oriented with respect to the region surrounding the cavity so that the two surfaces—the outer surface of the microelectrode and the surface of the surrounding region are substantially continuous. Typically the microelectrode is insulated from the distal tip so that the microelectrode is able to detect electropotentials generated by the body with high spatial resolution, independent of far-field signals picked up by the larger distal tip.

By configuring the microelectrode surface to conform with the distal tip surface, the overall surface in contact with the blood of the body cavity is substantially smooth, reducing the possibility of trauma to the tissue or blood clots forming during the ablation procedure.

System Description

Figure 1:
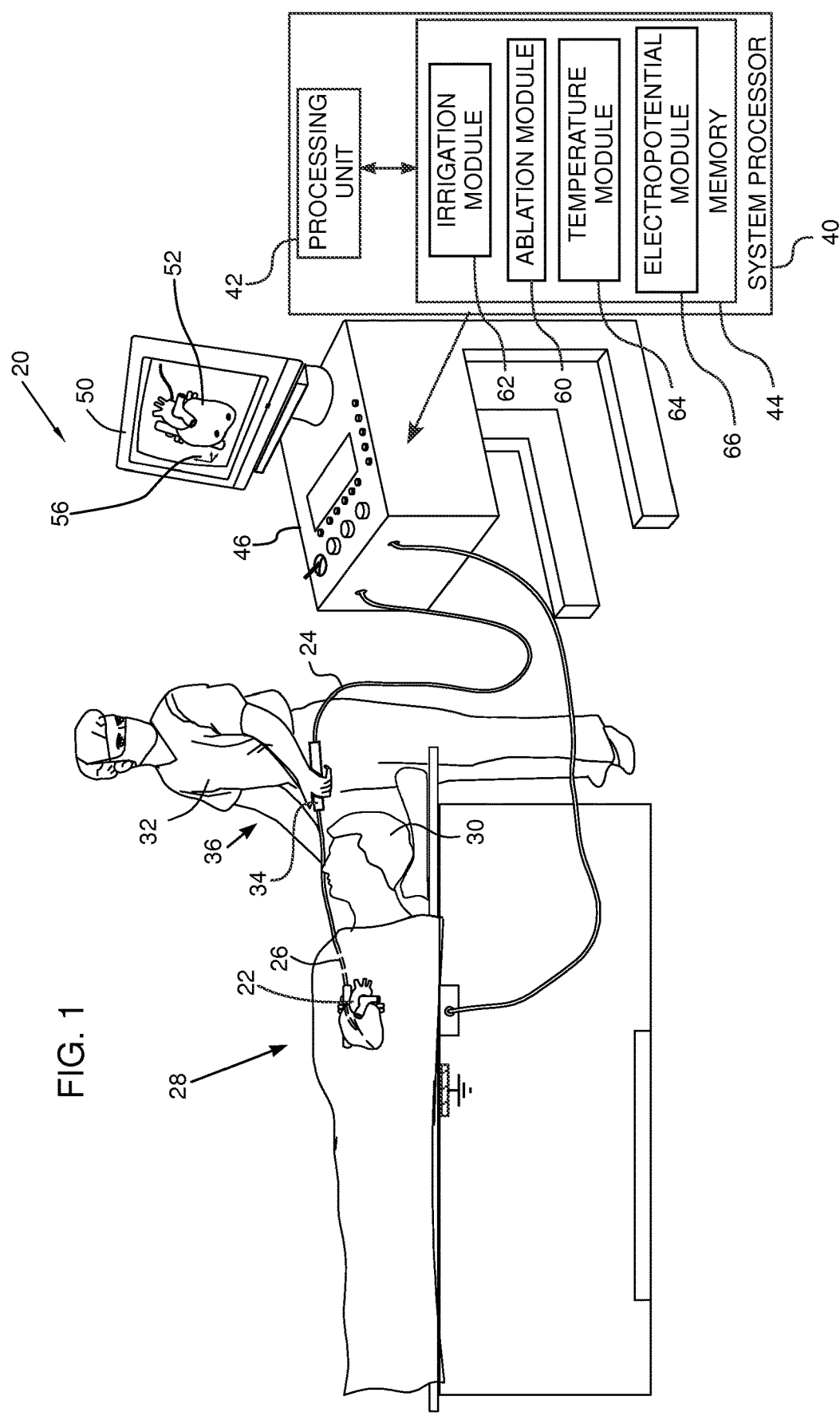
FIG. 1 is a schematic illustration of an ablation system, according to an embodiment of the present invention.

Reference is now made to FIG. 1, which is a schematic illustration of an ablation system 20, according to an embodiment of the present invention. System 20 is configured to perform ablation on a body organ during an invasive medical procedure, and/or to make measurements of physiological parameters, such as temperatures or electropotentials of the body organ, during the same or a different procedure. In the description herein the body organ, by way of example, is assumed to comprise a heart 22, although it will be understood that system 20 may be used on other body organs or cavities, such as the bladder or abdomen.

A catheter probe of system 20 comprises an insertion tube 24, having a distal end 26 which is inserted, using a handle 34, into the body of a subject 30. In some embodiments a high pass filter 36, described in more detail below, is incorporated into handle 34. A distal tip 28 of the insertion tube, described in more detail below, is implemented to act, inter alia, as an electrode for ablating tissue of heart 22 using radiofrequency (RF) energy. The ablation is assumed to be performed during a cardiac procedure performed by a user 32 of system 20 on the subject, and in the description herein the user of the system is assumed, by way of example, to be a medical professional.

System 20 may be controlled by a system processor 40, comprising a processing unit 42 communicating with a memory 44. Processor 40 is typically mounted in a console 46, which comprises operating controls typically including a pointing device such as a mouse or trackball. Professional 32 may use the pointing device to interact with the processor, which may be used to define a view of the heart presented by system 20 to the professional on a screen 50. The screen typically displays a three-dimensional (3D) map 52 of the internal surface of heart 22, typically together with items of auxiliary information related to the heart and/or the procedure and superimposed on the map.

In order to perform the ablation referred to above, memory 44 comprises an ablation module 60 which is able to generate RF energy at a power level and for a time period selected by professional 32, and to transfer this energy to the distal tip. Memory 44 also comprises an irrigation module 62, a temperature module 64, and an electropotential module 66, which enable professional 32 and system 20 to respectively control irrigation to the distal tip, monitor temperatures measured at the distal tip, and monitor electropotentials generated at the distal tip. As described below, distal tip 28 is structured, and/or comprises hardware elements, enabling the modules to operate.

System 20 is typically also implemented to track the position and orientation of the distal tip, and may also be implemented to perform other functions related to the medical procedure that the system is used for, such as measuring the force on the distal tip. To perform these functions the distal tip may also have appropriate hardware elements, such as location detectors and force sensors, which are operated by respective modules in memory 44. Tracking of a distal tip, and measurement of the force on the tip, are well known in the art, and are described, for example, in U.S. Pat. No. 8,456,182, and in U.S. Patent Applications 2011/0130648, 2007/0016007, the disclosures of which are incorporated herein by reference. For simplicity, hardware and modules associated with tracking and force measurement are not drawn in FIG. 1.

The software for operating system 20, including the software for the modules referred to above, may be downloaded to processor 40 in electronic form, over a network, for example, or it may, alternatively or additionally, be provided and/or stored on non-transitory tangible media, such as magnetic, optical, or electronic memory.

Figure 2B:
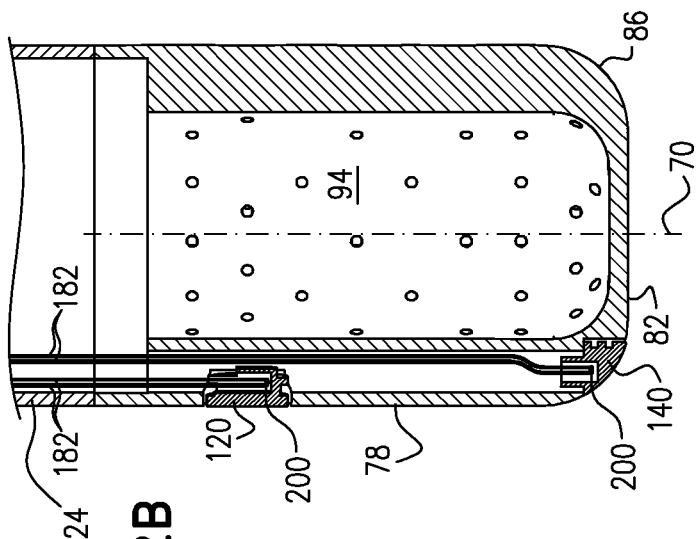
FIGS. 2A-2D are schematic illustrations of different aspects of a distal tip of an insertion probe used in the ablation system, according to an embodiment of the present invention.
Figure 2C:
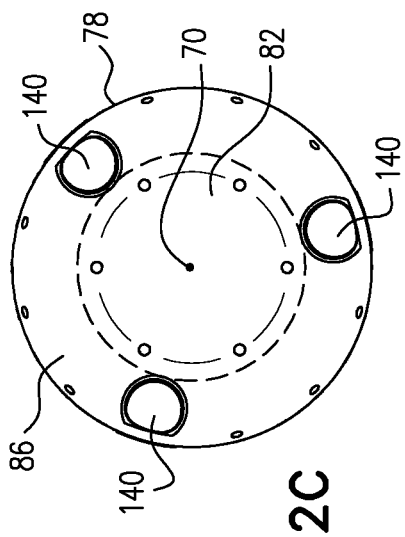
Figure 2A:
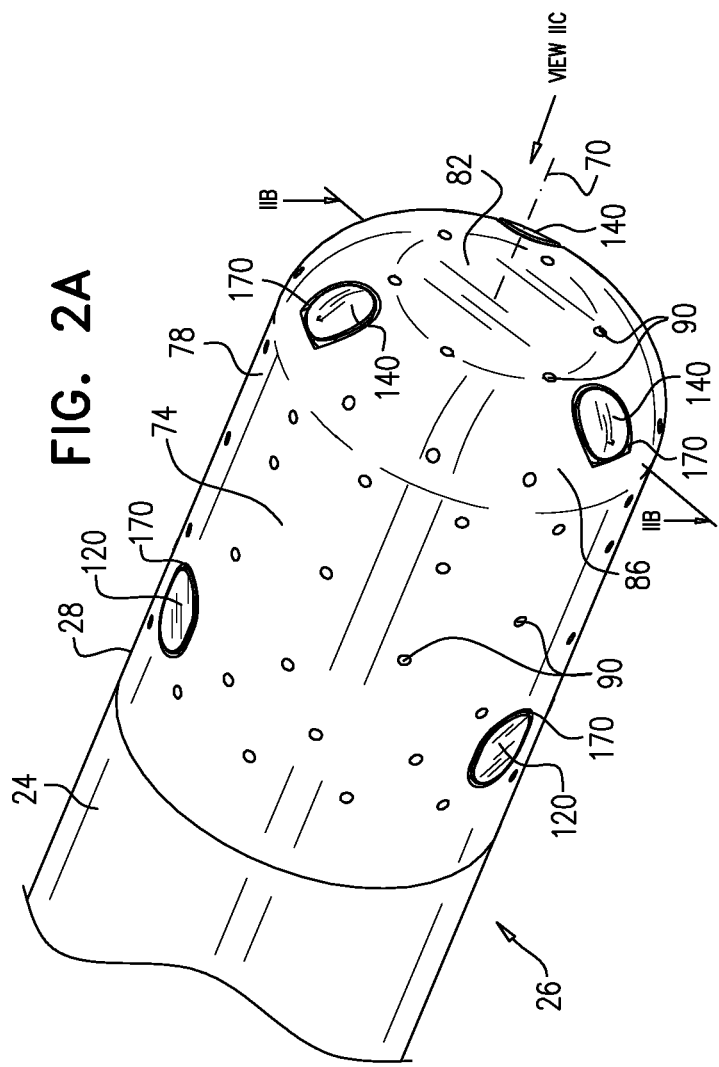
Figure 2D:
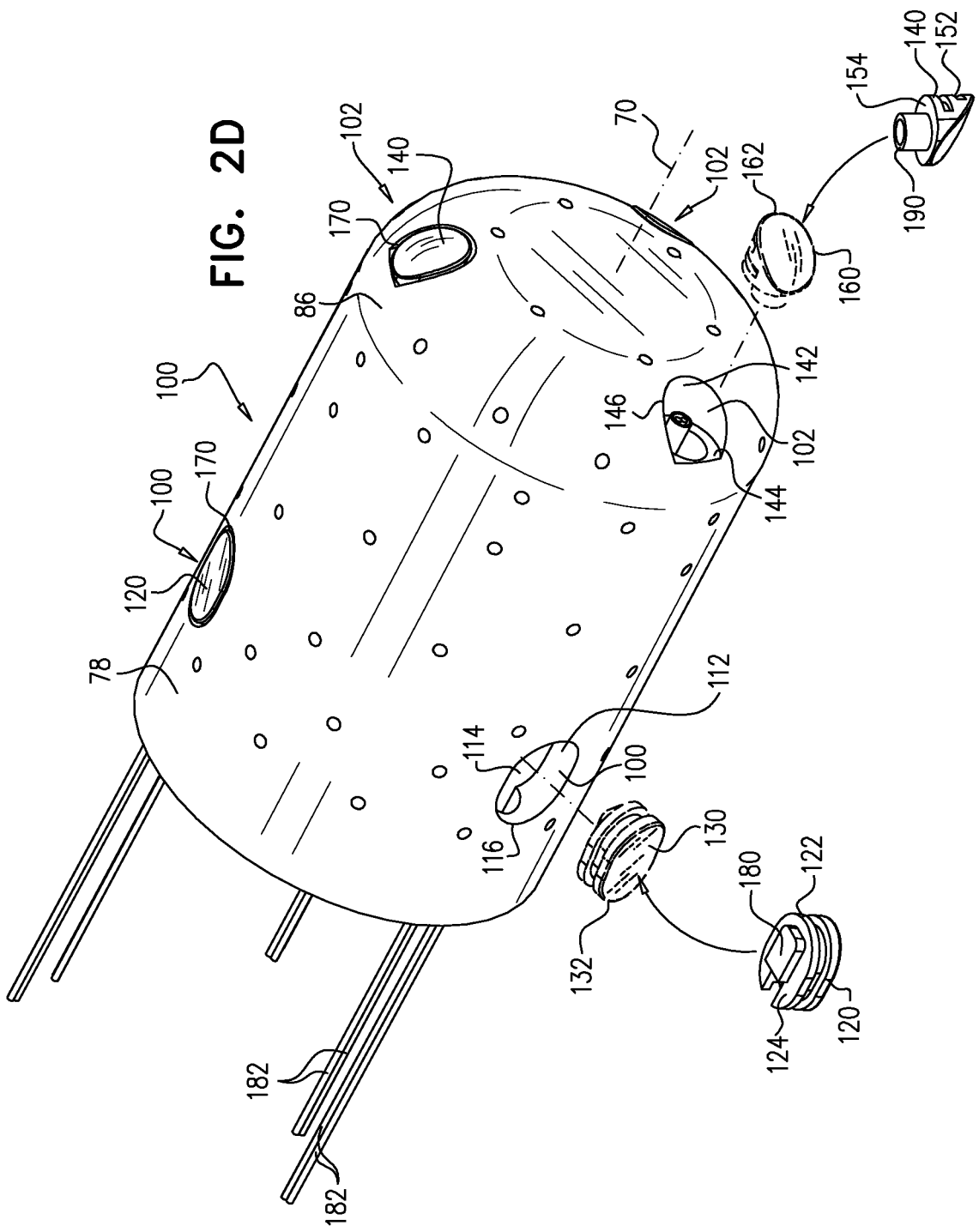

FIG. 2A is a schematic perspective illustration of distal end 26, FIG. 2B is a schematic cross-section of the distal end, FIG. 2C is a schematic view of the distal end from a point external to the distal end, and FIG. 2D is a schematic diagram illustrating assembly of the distal end, according to an embodiment of the present invention. As illustrated in FIG. 2A, insertion tube 24 terminates at distal tip 28, which is formed from a biocompatible conductor, such as platinum, palladium, gold, iridium, or an alloy of the aforementioned, and which has an axis of symmetry 70. The cross-section of the distal end illustrated in FIG. 2B is taken in a plane containing axis 70, and the view illustrated in FIG. 2C is taken looking towards the distal end along the axis.

An external surface 74 of distal tip 28 is divided into three regions: a cylindrical region 78 at the proximal end of the tip, a plane region 82 at the distal end of the tip, and a curved annular region 86 joining the cylindrical region to the plane region. Cylindrical region 78 is a surface of revolution of a line segment, parallel to axis 70, about the axis. Assuming the line segment is distant $r_c$ from the axis, the cylindrical region has a radius $r_c$.

Annular region 86 is a surface of revolution of a smooth curve about axis 70. The smooth curve terminates in two terminal points. At a first terminal point the curve has a tangent that is parallel to axis 70. At a second terminal point the curve has a tangent that is orthogonal to and that intersects the axis. In one embodiment the smooth curve comprises a section of a circle, but this is not a necessity, and the curve between the curve terminal points may be any smooth curve, having terminating tangents as described above, such as a section of an ellipse.

In the embodiment illustrated in the figures, distal tip 28 is penetrated by irrigation channels, so that surface 74 is pierced by irrigation apertures 90 that terminate the channels. Irrigation fluid, the flow of which is controlled by module 62, may be directed into the irrigation channels via an internal manifold 94 formed in the distal tip. The irrigation fluid for the manifold is provided by a dedicated conduit (not shown in the figures) within tube 24.

At least one cavity 100 is formed in the cylindrical region of external surface 74, and at least one cavity 102 is formed in the curved annular region of the external surface. The embodiment described herein comprises three cavities 100 which are distributed symmetrically with respect to axis 70, and three cavities 102 are also distributed symmetrically with respect to the axis. However, these numbers and distributions are purely by way of example, and embodiments of the present invention may have different numbers of cavities, and different distributions of the cavities, from those described herein. As described below, each cavity 100 is configured to accept and mate with a respective microelectrode 120 and each cavity 102 is configured to accept and mate with a respective microelectrode 140.

Considering cavity 100, in order to mate correctly with its microelectrode 120, the cavity has a cavity side surface 112, a receiving surface 114, and a cavity perimeter opening 116 where surface 112 intersects cylindrical region 78. Microelectrodes 120 are configured to be inserted into respective cavities 100, and in order to mate correctly with its cavity, each microelectrode has an external grooved surface 122 mating with cavity side surface 112, and a base surface 124 mating with receiving surface 114. In addition, microelectrode 120 has an external surface 130, described in more detail below, that has a microelectrode perimeter 132. After insertion, microelectrode perimeter 132 aligns with cavity perimeter opening 116. In addition to having the two perimeters align, in order that microelectrode 120 fits correctly into its cavity, surface 130 is contoured to conform with the curvature of the region surrounding its retaining cavity, i.e., the curvature of cylindrical region 78.

Considering cavity 102, in order to mate correctly with its microelectrode 140, the cavity has a cavity side surface 142, a receiving surface 144, and a cavity perimeter opening 146 where surface 142 intersects annular region 86. Microelectrodes 140 are configured to be inserted into respective cavities 102, and in order to mate correctly with its cavity, each microelectrode has an external grooved surface 152 mating with cavity side surface 142, and a base surface 154 mating with receiving surface 144. In addition, as for microelectrodes 120, each microelectrode 140 has an external surface 160, described in more detail below, that has a microelectrode perimeter 162. After insertion, microelectrode perimeter 162 aligns with cavity perimeter opening 146. In addition to having the two perimeters align, in order that each microelectrode 140 fits correctly into its cavity, surface 160 is contoured to conform with the curvature of the region surrounding its retaining cavity, i.e., the curvature of annular region 86.

Cylindrical region 78 and annular region 86 are examples of three-dimensional (3D) curved surfaces, and a general equation for such a surface is given by:

$$z=f(x,y), \quad (1)$$

where x, y, and z are variables plotted on mutually orthogonal axes, and where f is a function.

As is known in the art, the curvature of any point (x,y,z) on the surface defined by equation (1) is completely defined by the maximum and minimum curvatures, i.e. the principal curvatures, at the point, and these curvatures are orthogonal to each other. Furthermore, the values for the principal curvatures may be derived from the equation of the surface.

In the case of cylindrical region 78, an equation for the surface of region 78 may be represented by:

$$z=C(x,y), \quad (2)$$

where C is a function defining a cylindrical surface.

For region 78, since the region is a cylindrical surface, all points on the surface have the same principal curvatures, i.e., a minimum curvature of 0, and a maximum curvature, $k_{max}$, which is a positive, non-zero, value given by:

$$k_{max} = \frac{1}{r_c} \quad (3)$$

As stated above, for microelectrode 120 to fit correctly into its cavity, surface 130 of the microelectrode is a cylindrical surface that is contoured to conform with the curvature of region 78. Thus equation (2) is a common defining equation for surface 130 and region 78. In addition, since surface 130 is cylindrical and conforms with region 78, all points on surface 130 have a minimum curvature of 0 and a maximum curvature $k_{max}$.

In the case of annular region 86, an equation for the surface of region 86 may be represented by:

$$z=A(x,y), \quad (4)$$

where A is a function defining an annular surface of revolution.

For annular region 86, in contrast to cylindrical region 78, points on the surface of the annular region in general have different principal curvatures. However, since region 86 is a surface of revolution of a curve around axis 70, all points on the annular region a given distance from the axis have the same principal curvatures, although as the distance from the axis changes, at least one of the principal curvatures changes. In a disclosed embodiment, the curve that is revolved is an arc of a circle, in which case the surface of region 86 is toroidal.

For microelectrode 140 to fit correctly into its cavity, surface 160 of the microelectrode is contoured to conform with the curvature of region 86. Thus equation (4) is a common defining equation for surface 160 and region 86.

Each microelectrode 120 has a receptacle 180 which is configured to receive at least one conductive wire 182. Similarly, each microelectrode 140 has a receptacle 190 which is also configured to receive at least one conductive wire 182. Wires 182 are typically insulated so that they are electrically isolated from tip 28. In each case the wire is connected to the microelectrode, typically by soldering and/or welding. Each wire 182 is conveyed via tube 24 and handle 34 to processor 40, enabling potentials generated at the different microelectrodes to be measured by electropotential module 66.

In a disclosed embodiment, as is illustrated, two wires 182 of different materials are joined together, at a joint 200, to act as a thermocouple. The different materials may, for example, be copper and constantan. The joint is connected to the microelectrode within a single microelectrode receptacle, enabling potentials generated at the different microelectrodes to be measured by electropotential module 66, and the temperatures of the different microelectrodes to simultaneously be measured using temperature module 64.

In alternative embodiments, three wires 182, two being of different materials and joined to act as a thermocouple, are connected to a single receptacle. The third wire may be used to independently convey electropotentials to module 66. In some embodiments, the insulation between wires 182 and distal tip 28 is improved by enclosing the wires in insulating tubing, which may be made from any suitable insulator such as polyimide.

FIG. 2D illustrates schematically how the microelectrodes are assembled into tip 28. For simplicity and clarity, in FIG. 2D wires 182 are not shown as being connected to their respective microelectrodes. Prior to insertion into their respective cavities, the microelectrodes may be coated with a biocompatible insulating plastic, such as parylene, so that after insertion the microelectrodes are electrically insulated from the distal tip. After insertion the plastic may be removed from surfaces 130 and 140, leaving a thin layer 170 of insulation between a given microelectrode and the distal tip.

In operation of system 20, ablation module 60 generates radiofrequency (RF) ablation energy, typically at a frequency of the order of 480 kHz, and the RF energy, after transmission to tip 28, is used to ablate a region of the body cavity in contact with the tip. Simultaneously, electropotential module 66 is able to independently monitor electropotentials of the body cavity section, from signals acquired by microelectrodes 100 and 102 in contact with the region. Insulation layer 170 ensures that there is no interference between the microelectrode signals and the RF ablation energy, and also provides high spatial resolution electrograms. If thermocouples have been attached to the microelectrodes, as described above, temperatures of the body cavity region may also be simultaneously and independently monitored.

The electropotential and/or thermocouple signals generated at the microelectrodes are relatively low frequency signals, of the order of 1 kHz or less. In some embodiments high pass filter 36 (FIG. 1) may be connected between the microelectrodes and the distal tip, or between wires 182 and a conductor conveying the ablation RF energy to the distal tip. The filter may be configured to transfer RF ablation energy to the microelectrodes, while preventing the low frequency thermocouple and/or electropotential signals on wires 182 from being interfered with, so that surfaces 130 and 160 of the microelectrodes may also be used for ablation. As illustrated in FIG. 1, high pass filter 36 may be conveniently located in handle 34.

The description above has assumed that microelectrodes are inserted into cavities of specific regions of the distal tip, and that the distal tip has a particular shape. It will be appreciated that embodiments of the present invention may be applied to other shapes of distal tip, so that, for example, the regions of the distal tip, and/or the whole of the distal tip, does not need to be a surface of revolution. As for the embodiments described above, for regions that are not surfaces of revolution the surface of the microelectrode is contoured, located and oriented to conform with the curvature of the region surrounding the cavity into which the microelectrode is inserted.

It will thus be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

We claim:

1. Apparatus, comprising:
a processor having a temperature module and an electropotential module;
an insertion tube, configured to be inserted into a body cavity;
a distal tip electrode having a cylindrical region defining a longitudinal axis connected to the insertion tube, the distal tip electrode having an external surface and a cavity formed in the external surface, the cavity being surrounded by a region of the external surface having a curvature;
a microelectrode inserted into the cavity, the microelectrode configured to detect electropotentials generated by the body cavity, the microelectrode having a distal surface, and being configured to fit into the cavity so that the outer surface of the microelectrode is contoured, located and oriented to conform with the curvature of the region such that all points on the external surface of the distal tip electrode and the distal surface of the microelectrode located at the same radial distance from the longitudinal axis have a same principal curvature, but all points on the external surface of the distal tip electrode and the distal surface of the microelectrode located at a different radial distance from the longitudinal axis have a different principal curvature; and
two conductors of two different materials connected at a junction to form a thermocouple, and wherein the junction is connected to the microelectrode at a single microelectrode receptacle so as to provide a signal representative of a temperature of the microelectrode to the temperature module through the two conductors, and wherein the processor and at least one of the two conductors is configured to allow electropotentials generated by the body cavity at the microelectrode and the signal generated by the thermocouple representative of the temperature of the microelectrode to be measured simultaneously by the processor.

2. The apparatus according to claim 1, wherein the external surface of the distal tip electrode and the outer surface of the microelectrode are defined by a common equation.

3. The apparatus according to claim 1, and comprising insulation located so as to electrically insulate the microelectrode from the distal tip.

4. The apparatus according to claim 1, wherein the distal tip electrode is configured to receive radiofrequency (RF) energy at an ablation frequency adapted to perform ablation on the body cavity.

5. The apparatus according to claim 4, wherein the microelectrode is configured to detect an electropotential at a lower frequency than the ablation frequency.

6. The apparatus according to claim 5, and comprising a high pass filter, configured to block the lower frequency and to pass the ablation frequency, coupling the microelectrode to the distal tip.

7. The apparatus according to claim 6, and comprising a handle configured for a user of the apparatus to hold the insertion tube, wherein the high pass filter is located within the handle.

8. The apparatus according to claim 1, wherein the external surface and the distal surface of the microelectrode have a common surface of revolution.

9. The apparatus according to claim 1, wherein the cavity has a first cavity side surface intersecting the annular region, and a receiving surface extending at an angle from the cavity side surface.

10. The apparatus according to claim 9, wherein the microelectrode has an external surface mating with the first cavity side surface and a base surface mating with the receiving surface.

11. The apparatus according to claim 10, wherein the cavity has a second cavity side surface that has a diameter smaller than a diameter of the first cavity side surface.

12. The apparatus according to claim 11, wherein the microelectrode has a receptacle protruding from the base surface, the receptacle being configured to receive at least one conductive wire within the receptacle.

* * * * *